United States Patent [19]

Gibboni et al.

[11] Patent Number: 5,447,689
[45] Date of Patent: Sep. 5, 1995

[54] METHOD AND APPARATUS FOR FLOW CONTROL

[75] Inventors: David J. Gibboni, Havertown, Pa.; Susan M. McGeehan, Woodbury, N.J.; Wai T. Law, Sewell, N.J.

[73] Assignee: Actimed Laboratories, Inc., Burlington, N.J.

[21] Appl. No.: 203,565

[22] Filed: Mar. 1, 1994

[51] Int. Cl.⁶ ............................................. C01N 30/50
[52] U.S. Cl. .................................. 422/56; 427/2.11; 422/58
[58] Field of Search .................. 8/115.6; 427/2; 422/56–58

[56] References Cited

U.S. PATENT DOCUMENTS

| | | |
|---|---|---|
| 3,723,064 | 3/1973 | Liotta . |
| 4,038,485 | 7/1977 | Johnston et al. . |
| 4,144,306 | 3/1979 | Figueras ............................ 422/56 |
| 4,241,136 | 12/1980 | Dereser . |
| 4,310,399 | 1/1982 | Columbus ........................... 422/58 |
| 4,416,777 | 11/1983 | Kuroda et al. .................... 436/177 |
| 4,522,786 | 6/1985 | Ebersole ............................ 422/56 |
| 4,522,923 | 6/1985 | Deutsch et al. .................. 436/536 |
| 4,549,952 | 10/1985 | Columbus ......................... 422/100 |
| 4,587,099 | 5/1986 | Rothe et al. ....................... 422/56 |
| 4,587,102 | 5/1986 | Nagatomo et al. ................. 422/56 |
| 4,615,983 | 10/1986 | Koyama ........................... 436/514 |
| 4,618,476 | 10/1986 | Columbus ......................... 422/100 |
| 4,738,823 | 4/1988 | Engelmann ........................ 422/56 |
| 4,774,192 | 9/1988 | Terminiello et al. ............... 436/530 |
| 4,837,395 | 6/1989 | Leeder et al. ...................... 435/14 |
| 4,876,067 | 10/1989 | Deneke et al. ..................... 422/56 |
| 4,889,797 | 12/1989 | Amano et al. ....................... 436/4 |
| 4,923,680 | 5/1990 | Nelson ................................ 422/58 |
| 4,959,305 | 9/1990 | Woodrum ........................... 422/56 |
| 4,959,324 | 9/1990 | Ramel et al. ...................... 436/169 |
| 4,963,498 | 10/1990 | Hillmann et al. ................... 436/69 |
| 4,966,784 | 10/1990 | Tanaka et al. ....................... 427/2 |
| 5,028,236 | 7/1991 | Kortmann et al. ................ 8/128.1 |
| 5,051,237 | 9/1991 | Grenner et al. .................... 422/56 |
| 5,071,675 | 12/1991 | Gupta et al. ...................... 427/213 |
| 5,089,383 | 2/1992 | Leeder et al. ...................... 435/7.9 |
| 5,104,812 | 4/1992 | Kurn et al. ........................ 436/165 |
| 5,185,127 | 2/1993 | Vonk .................................. 422/56 |
| 5,207,988 | 5/1993 | Lucas .................................. 422/73 |
| 5,213,965 | 5/1993 | Jones ................................... 435/11 |
| 5,217,905 | 6/1993 | Marchand et al. ................ 436/518 |

OTHER PUBLICATIONS

Bunce et al, *Disposable Analytical Devices Permitting Automatic, Timed, Sequential Delivery of Multiple Reagents*, Analytical Chemical ACTA, vol. 249, pp. 263–269, 1991.

Bernstein, *Lowering Blood Cholesterol to Prevent Heart Disease*, Journal of the American Medical Association, vol. 253, No. 14, pp. 2080–2086, Apr. 12, 1985.

Primary Examiner—James C. Housel
Assistant Examiner—Rachel Freed
Attorney, Agent, or Firm—Iver P. Cooper

[57] ABSTRACT

Sizing materials are applied to porous substrates to retain fluids in the substrate for a discrete period of time. After that time period, the fluid is substantially completely released from the porous substrate. Sizing materials include alkyl ketene dimers, fluorocarbon resins, and fatty acid chlorides.

25 Claims, 4 Drawing Sheets

SIZED PAPER

FREE ROTATION AT ANCHOR

METHOD AND APPARATUS FOR FLOW CONTROL

FIELD OF THE INVENTION

The present invention relates to methods and apparatus for controlling the flow of fluids through a substrate such as a pad or filter, particularly for use in clinical assay devices.

BACKGROUND OF THE INVENTION

The ability to measure a wide variety of physiologically active compounds, both naturally occurring and synthetic, has become of increasing importance, both as an adjunct to diagnosis and to therapy. While for the most part, assays of physiological fluids and drugs have required clinical laboratory determinations, there is an increasing awareness of the importance of being able to carry out assay determinations in the physician's office or in the home. To be able to perform an assay in a physician's office or home requires that the assay have a simple protocol and be relatively free of sensitivity to small changes in the conditions under which the assay is carried out.

A wide range of disposable assay devices has been developed for use either in analytical laboratories or in physicians' offices or homes. These devices, because they are used by inexperienced operators, should be simple to operate and should incorporate all the reagents necessary for the test to be conducted.

One analyte of importance is cholesterol. There is a clearly established relationship between total blood cholesterol (mainly the LDL fraction) and coronary artery disease (*J.A.M.A.* 253: 2080-2086, 1985). New guidelines have been established for adults to identify risk groups associated with blood cholesterol levels. Since cholesterol levels can be controlled by both diet and cholesterol-lowering medications, it is useful for those individuals at risk to be able to monitor their own cholesterol at home in order to reduce the potential for heart disease. The measurement of other naturally occurring compounds of physiological importance, such as glucose, lipoproteins, etc., as well as synthetic drugs, is also of great interest. For example, therapeutics, drugs of abuse, iodothyronines, alcohol, cytokines, as well as numerous other chemical analytes could be monitored. Also of interest are microorganisms, $\beta$-HCG for ectopic births, antibodies associated with disease, and the like.

Many of the most commonly used assays in disposable assay devices require an incubation step, such as requiring enzymes to act on the sample, such as for determinations of cholesterol, glucose, uric acid, and the like. Additionally, enzymes are often used as labels in immunoassays. In a conventional enzyme immunoassay, an enzyme is covalently conjugated with one component of a specifically binding antigen-antibody pair, and the resulting enzyme conjugate is reacted with a substrate to produce a signal which is detected and measured. The signal generated by the enzyme, in either the conventional chemical assay or the immunoassay, may be a color change, and the color change may be detected with the naked eye or by a spectrophotometric technique.

Many of the disposable assay devices currently in use include one or more reagent zones comprising layers incorporated with assay reagents. Among the problems encountered in use of these devices is the premature interaction or migration of these reagents, either during the manufacturing process or upon introduction of the sample to the device. Both enzymatic and chemical reactions often require incubation steps. One of the challenges in designing a truly "one-step" disposable device is to provide a means to delay the fluid flow in order to allow for proper incubation periods. This is particularly challenging for non-instrumented disposable analytical devices.

Ideally, a disposable assay device should include a means to delay the flow of the sample through the device for a predetermined time to permit incubation of the sample with the reagents or indicators present in a particular region of the device. After the incubation period, which is generally on the order of a few minutes or less, the sample then flows to the next region of the device for further processing.

An ideal flow delay means should work like a valve, with a "closed" and an "open" state. When the state is "closed", the fluid flow should stop, and when the state switches to "open", the fluid should flow through the flow-delay valve with little or no restriction, and the flow rate of the fluid through the device should be unchanged.

A wide range of disposable analytical devices has been developed which include means to control flow of fluids therethrough. However, none of these previously developed devices has a flow-delay means with a valve-like effect on the flow of fluids.

Deutsch et al., in U.S. Pat. No. 4,522,923, disclose a test device comprising a container having at least two water-soluble barriers between at least three superposed chambers. Upon introduction of an aqueous biological sample to be tested into the topmost chamber, the sample will successively mix with the contents of the chambers. The contact time in each chamber is a function of the water solubility of the barriers.

Ebersole, in U.S. Pat. No. 4,522,786, discloses a multilayer test device comprising at least two liquid permeable functional layers superposed upon one another, the layers in liquid communication, with a barrier layer separating the layers. The barrier layer is a chemically inert, liquid insoluble, foraminous septum, the foramina of which are filled with a thermally sensitive material which is liquid impermeable at assay temperatures but capable of melting when heated to provide rapid liquid communication between the function layers. This melted material then travels through to the next layer with the test liquid.

Jones, in U.S. Pat. No. 5,213,965, discloses an assay device for measuring high density lipoprotein or cholesterol in a fluid sample which contains other lipoproteins. Sieving materials chromatographically separate aggregated from non-aggregated materials in the sample as the sample flows through the matrix. A reagent reservoir slowly releases a precipitating agent into the matrix by formulating the precipitating agent with a binder for slow dissolution on contact with a sample. There is no provision for timing the delay of the sample within a region.

Vonk, in U.S. Pat. No. 5,185,127, discloses a device for assaying an analyte comprising an enclosure and a filter stack. Flow control is provided by a hydrophilic membrane which contains a binder for an analyte. This membrane is impervious to the passage of an aqueous liquid until activated by a wetting agent.

Johnston et al., in U.S. Pat. No. 4,038,485, disclose a test composition for detecting a component in a sample which comprises a reactant system which, upon contact with the sample, interacts with the component to produce a detectable response, as well as an inhibitor system which, upon contact with the sample, prevents the reactant system from interacting with the component after lapse of a predetermined time.

Amano et al., in U.S. Pat. No. 4,889,797, disclose a dry analytical element for assaying enzyme activity in a liquid comprising a support having provided thereon at least a porous liquid-spreading layer composed of fibers which do not absorb water. Here, flow control is directed to decreasing spreading of the liquid within a layer rather than through a layer.

Deneke et al., in U.S. Pat. No. 4,876,076, disclose an assay device comprising a first carrier layer having applied thereto a liquid absorbing layer and a separate second movable carrier having applied thereto a dissolvable reagent-containing layer which is not in initial contact with the first carrier layer. The reagent-containing layer is dissolved by contact with a liquid contained in the liquid absorbing layer, and the first carrier layer is positioned in the device to permit contact between the liquid absorbing layer and the reagent-containing layer by applying pressure to one of the carrier layers. Flow of sample from one layer to another is controlled by bringing the two carrier layers into contact with each other so that the sample is transferred. This type of flow control is also shown in Ramel et al., U.S. Pat. No. 4,959,324, in which a flow path is completed by moving a sample receiving pad into a gap between two assay strips.

Woodrum, in U.S. Pat. No. 4,959,305, discloses a multizone test device for immunoassays in which assay reagents are reversibly immobilized within the various layers of the device. The binding interactions within the device depend upon the interactive properties of and between the assay reagents and the matrix comprising the incorporating layer of the reversibly immobilized assay reagents, and the disruptive properties of the liquid test sample necessary to disrupt the particular reversible binding interaction between the assay reagents and the matrix to release and render useable the reagents in an analytically effective amount within the device.

Columbus, in U.S. Pat. No. 4,549,952, discloses a liquid transport device having means for increasing the viscosity of the liquid when the liquid flows past at least one surface of the device. Control of flow is achieved strictly through viscosity increase.

Hydration and expansion of a compressed foam switching element permit automatic timed sequential delivery of multiple reagents in a device disclosed by Bruce et al. in *Analytical Chemical Acta* 249 (1991), 263–269. This technique is not well-suited for devices that require no diluent and which are sensitive to the total volume of sample fluid required.

Hillmann et al., in U.S. Pat. No. 4,963,498, disclose methods for using specific binding pair members which result in agglutination formation. The resulting agglutinated particles may provide for changes in flow rate.

Interrupting capillary flow of liquid between two pieces of bibulous material using a liquid expandable material is shown in Kurn et al., U.S. Pat. No. 5,104,812.

Physical barriers to reduce the flow rate in a zone of a liquid transport zone are shown in Columbus, U.S. Pat. No. 4,310,399; Columbus, U.S. Pat. No. 4,618,476; and Grenner et al., in U.S. Pat. No. 5,051,237.

Liquid flow through a filter can also be controlled by reactions between the sample and a component of the filter, cf. U.S. Pat. No. 5,217,905, to Marchand et al. Similarly, Tanaka et al., in U.S. Pat. No. 4,966,784, disclose inhibiting migration of a water-soluble indicator in a reagent layer in an assay device by using a particular organic solvent.

Liotta, in U.S. Pat. No. 3,723,064, discloses a layered testing device including a first porous layer impregnated with a reagent system which reacts with the analyte to produce an end product. A membrane having plural regions with differing permeabilities is adjacent to the first porous layer. The permeability differences are obtained either by impregnating the regions with different concentrations of a chemical reactive with the end product, or by varying the pore size in the regions.

Engelmann, in U.S. Pat. No. 4,738,823, discloses a test strip which has a preselected capacity for absorbing sample. In this case, however, the amount of sample applied to the test strip is metered, rather than the amount of sample fluid that is retained for a predetermined time within a selected area of a test device.

Other workers have coated filters with a variety of coatings to alter conditions within the filter, none of which provides a valve-like action to control the flow of fluid: Nagatomo et al., U.S. Pat. No. 4,587,102.

A layer for controlling diffusion rate of sample through the device can be provided by varying the formulation ratio of a hydrophobic polymer and a hydrophilic polymer which constitute the layer, as shown by Koyama et al., U.S. Pat. No. 4,615,983. In a similar fashion, Rothe et al., in U.S. Pat. No. 4,587,099, disclose a test strip which includes a slowly absorbent layer for sucking up a fluid sample. This layer is slowly absorbent rather than a layer which retains a liquid for a predetermined period of time.

A flow-delaying polymer on an immunoassay filter is shown in Nelson, U.S. Pat. No. 4,923,680.

Blood clotting has been used to inhibit sample flow through a track in Lucas, U.S. Pat. No. 5,207,988.

Leeder et al., in U.S. Pat. Nos. 4,837,395 and 5,089,383, disclose a heterogeneous immunoassay in which the production of the signal is temporarily delayed by using an inhibitor which can be an alternate substrate for the enzyme signal or a compound which reacts with the product of the enzyme and its substrate.

Terminiello et al., in U.S. Pat. No. 4,774,192, disclose a dry chemistry reagent system comprising a porous membrane of essentially uniform composition which has a porosity gradient from one planar surface thereof to the other.

Kuroda et al., in U.S. Pat. No. 4,416,777, disclose a material for separating leukocytes from a leukocyte-containing suspension which comprises a fibrous material having a surface layer coated on the fibrous material which can be dissolved by degrees in water.

None of the above-noted patents provides a reliable means for metering the rate of flow delay through a layer in order to retain a sample in contact with a reagent for a predetermined length of time, nor where the length of time can be varied depending on the incubation time required by the assay.

Alkyl ketene dimers have been used for many years as reactive alkaline sizing agents in the paper industry. Industrially, alkyl ketene dimers are added to the "wet end" of the papermaking process, that is, the slurry of bleached pulp in water that is at the very start of the papermaking process. Aqueous alkyl ketene dimer emulsions, which contain alkyl ketene dimer and additives such as defoamers and biocides, have been developed and marketed for this application. Wet-end addition allows for thorough deposition of the alkyl ketene dimer throughout the cellulose fiber, and is a less costly process than post-treatment of the fibers.

Gupta et al., in U.S. Pat. No. 5,071,675, disclose sizing cellulose fibers by applying a solution of alkyl ketene dimer in ethanol to cellulose fibers. Kortmann et al., in U.S. Pat. No. 5,028,236, disclose treating wool and synthetic polyamide materials with ketene dimers. Dereser, in U.S. Pat. No. 4,241,136, discloses a cationic size composition for glass fibers based upon a cationic film-forming polymer which also includes an alkylketene dimer. The coated glass fibers are then coated with an anionic size composition containing an anionic film-forming polymer whereby the cationic and anionic polymers react to form a thin film on the glass fibers.

No admission is made that any of the patents cited above constitutes prior art.

SUMMARY OF THE INVENTION

The present inventors have discovered a number of sizing materials that can be applied to fibrous substrates, such as pads, so as to provide a flow delay means with a valve-like effect on the flow of fluids. The retention period can range from less than one minute to more than 20 minutes, depending upon the fluid, the impregnant or coating (sizing) material, and the amount of impregnant or coating material applied to the substrate. For the purpose of the present invention, a sizing material is a material which is applied to a surface to change the properties of the surface. More particularly, in the present invention the sizing material inhibits the absorption of fluids onto the surface which has been treated with the sizing material for a predetermined period of time. After a given time in which the fluid is retained on the substrate, the fluid all flows through the substrate, often onto an adjoining layer, which adjoining layer quickly absorbs the fluid. This provides a valving action for the fluid in which the valve is closed for a predetermined time and then opened to permit fluid to flow through. For the present invention, a flow control means is a substrate which has been treated, coated, or impregnated with a sizing material which retains a liquid sample in the substrate for a predetermined period of time, after which time substantially all of the liquid sample flows through the substrate.

The sizing material is preferably an alkyl ketene dimer. None of the prior workers has used alkyl ketene dimers for anything other than coating agents for papers, and there has been no recognition that by controlling the amount of alkyl ketene dimer applied to a substrate one can retain fluid in the substrate for a predetermined discrete period of time. After a certain period of time, depending upon the liquid and the amount of sizing material on the substrate, the liquid seeps through the substrate as if the substrate were unsized. The impregnant thus acts as a flow valve, in that it retains the fluid in the substrate for a time certain, and then releases all of the fluid from the substrate.

Other sizing materials that can be used in the present invention as sizing materials include fatty acid chlorides and fluorocarbon resins.

The flow control means of the present invention has the following features and advantages:

The degree of flow control means is readily metered by the amount of sizing material applied to the substrate.

The coated or impregnated substrates are self-regulating, and require no designed-in moving parts and no input from the user for accurate operation.

Different types of reactions that require different incubation times can all use the same type of pad with differing types and/or levels of sizing material applied corresponding to the desired flow delay.

The delay times obtained are highly reproducible.

The sizing materials used for flow delay are inexpensive and are easily and accurately dispensed onto the substrate material.

The sizing materials do not chemically affect reagents used in clinical assays.

The sizing materials used do not affect the viscosity of the reagent fluid and thus do not affect the flow of the reagent fluid or the run time of the reagent strip portion of the device.

Some of the sizing materials can be covalently attached to the substrate, particularly if the substrate is paper or a surface-modified glass fiber material.

DETAILED DESCRIPTION OF THE PREFERRED EMBODIMENTS

Figure 1:
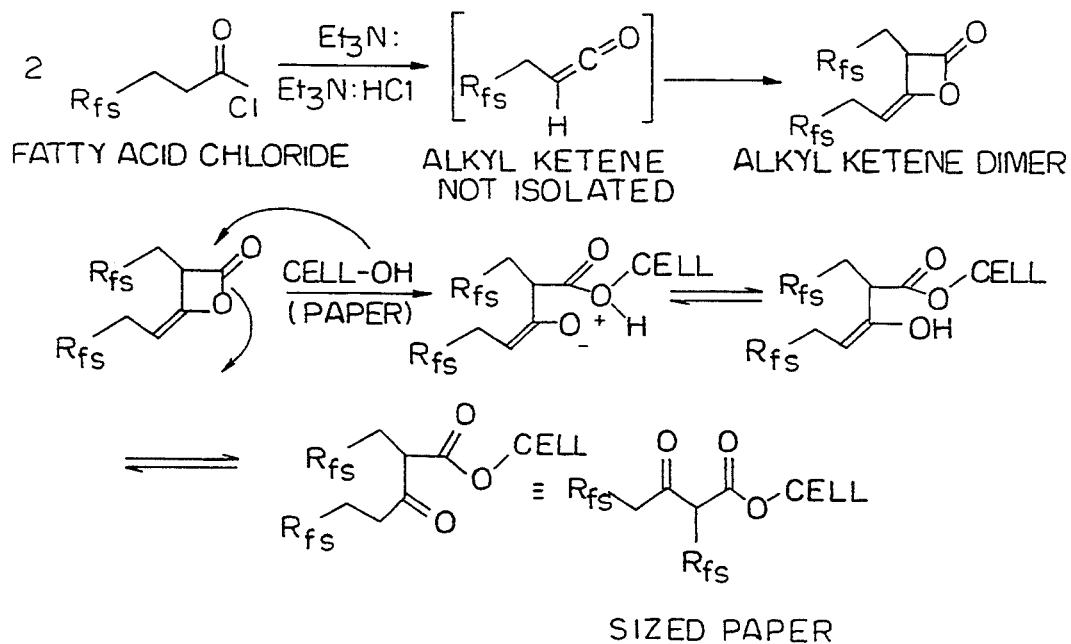
FIG. 1 shows the reaction of alkyl ketene dimer with cellulose.

The present invention provides a coating of a sizing material on a substrate to inhibit flow of a liquid through the substrate for a predetermined period of time. After a predetermined period of time, the liquid is completely released through the substrate. There is substantially no effect on the viscosity and flow characteristics of the fluid nor on the chemical composition of the fluid. The rate of flow delay, i.e., the length of time the liquid is retained on the substrate, is controlled by the amount of sizing material applied to the substrate. Thus, one can control the length of time that the flow is delayed by varying the type and amount of sizing material. The control means is self-regulating.

More particularly, a sizing material is applied to a pad made of paper, glass fiber, fabric, or similar porous materials to provide flow-control means for use in diagnostic devices. These pads retain fluid for a discrete period of time to enable substances in the fluid to react with components in the pad for a discrete period of time, after which the fluid flows completely through the pad. Different types of reactions that require different incubation times can all use the same type of pad with differing levels or different types of sizing material applied to correspond to the desired delay time. Unlike many coating materials heretofore used in assay device pads, the sizing materials do not chemically affect the reagent mixture, nor do they affect the viscosity of the sample or reagent fluid. The sizing materials of the present invention thus do not affect the flow of the reagent fluid or the run-time of a reagent strip portion of an assay device.

For the purpose of the present invention, "flow delay" means that the flow of a fluid through a material is delayed for a certain length of time, after which the fluid flows substantially completely through the flow delay. For example, for the critical period of time, $t_c$, from introduction of the sample, $t_0$, to $t_c$, the flow rate is such that in this time period no more than 10%, and preferably no more than 5%, of the sample flows through the material. After $t_c$, substantially all of the remainder of the sample passes through the flow delay material. Moreover, the rate of flow after $t_c$ should be substantially greater than the rate of flow before $t_c$, as the sizing material does not increase the viscosity of the sample.

As different reactions require different incubation times, $t_c$ preferably ranges from 2 seconds to twenty minutes. $t_c$ more preferably ranges from about 2.5 seconds to about 5 minutes. Particularly for quantitative assays, the amount of sample retained in the flow delay material must be a sufficient amount of sample to be incubated in the flow delay material to effect a valid assay. Likewise, the amount of sample which passes through the flow delay material must be a sufficient amount of sample to effect a valid assay.

The flow delay means of the present invention, in other words, acts like a timed valve, in that the fluid is retained in the flow delay means for a predetermined time, $t_c$. After this time $t_c$, the fluid flows substantially completely through the flow delay means, such as into an adjoining layer of an assay device.

Once the flow delay means has "opened" to the fluid, at $t_c$, it is important that substantially all of the fluid flow through the flow delay means rather than remain in the flow delay means. The flow delay means retains the fluid in the flow delay area only for a predetermined time, and then permits the fluid to flow through the flow delay means substantially without changing the fluid. The flow delay means does not affect the viscosity of the fluid, nor does the flow delay means add extraneous material to the fluid sample from the flow delay means. The fluid is free to flow directly through the flow delay means just as if a mechanical valve had been opened, and substantially all of the fluid flows through this "valve" without being retained in the flow delay means.

One way of expressing the fluid flow through the flow delay means is in terms of the time required for the sample to pass completely through the flow delay means once the predetermined time, $t_c$, has passed. The time period from initial contact of the fluid sample with the flow delay means, $t_0$, to the predetermined time, as noted above, can be expressed as $t_c$. The time required for the sample to flow through the flow delay means after $t_c$ can be expressed as $t_f$. Ideally, $t_f$ should not be much greater than $t_c$, and may often be smaller than $t_0$, depending upon the length of time the sample is retained by the flow delay device, the nature of the sample, and subsequent operations to be performed on the sample.

For example, if $t_c$ is one minute, $t_f$ can be from less than one minute to greater than five minutes, depending upon the initial viscosity of the sample, the rapidity with which the test must be conducted, and the like. On the other hand, if $t_c$ is 20 minutes, it may be useful for $t_f$ to be less than 20 minutes. Depending upon the type of sample applied to the flow delay means and the rate at which one desires the sample to flow through the device, one can adjust $t_c$ and $t_f$ so that they are multiples of each other. One skilled in the art can readily determine the relationship between $t_c$ and $t_f$ which is optimum for the particular fluid sample to be treated, and can adjust the flow delay means accordingly.

In another example, with a relatively viscous fluid sample which only requires an incubation of one minute, $t_c$ can be one minute and $t_f$ can be up to about ten minutes. On the other hand, for a relatively free-flowing sample which requires a long incubation period, such as 20 minutes, $t_f$ can be a fraction of $t_c$, i.e., 5 minutes, or ¼ $t_c$. The relationship between $t_c$ and $t_f$ is not critical to the invention; the criticality is that the flow delay means act as a means to retain the fluid sample for a predetermined time, and then release the sample through the flow delay means.

A great many sizing materials can be used to control the flow of liquids through substrates, depending upon the type of fluids used. Examples of these sizing materials include alkyl ketene dimers, alkenyl succinic anhydrides, and fluorocarbon resins, either alone or with other materials such as saccharides, including mono-, di-, or oligosaccharides, including lactose, sucrose, glucose, etc.; low molecular weight polymers, generally of molecular weight of from about 500 to 20,000, such as polyethylene glycol (PEG); waxes and the like. Other polymers include polyvinyl pyrrolidone, polyvinyl alcohol, modified soluble cellulosics such as carboxymethylcellulose, cellulose acetate, hydroxyethylcellulose, and the like, and proteinaceous polymers like gelatin. Since not all materials offer equivalent degrees of fluid retention, the sizing material and amount thereof used to coat or impregnate the substrate can be chosen to provide the desired flow delay time for the fluid to be controlled.

A wide range of disposable analytical devices has been developed which can incorporate the flow delay device of the present invention. These devices incorporate all of the components needed for an assay in a wet or a dry format. Many of these devices receive samples of whole blood and perform blood separation, mixing, incubation, addition of reagents, and signal generation by one or more manipulation steps, optionally using small instruments. However, it is desirable to perform many assays using disposable devices which do not require instrumentation or additional equipment. Since chemical and enzymatic reactions often require incubation, an assay device in which an incubation step is required must have means to delay flow of fluid through the device in order to allow for proper incubation periods. Ideally, the flow delay means should function like a valve, with both a closed state in which the fluid flow stops, and an open state, in which the fluid flows through the flow-delay means with little or no restriction. Once the flow delay means is in the open state, the flow rate of the fluid through the device should be unchanged.

Samples and Analytes

The flow delay means of the present invention can be used in assays for a great many different types of fluid samples. The fluid sample containing the analyte to be determined can be a naturally occurring or artificially formed fluid suspected of containing the analyte, such as a biological fluid. Examples of such fluids include biological fluids such as blood, plasma, serum, urine, milk, saliva, amniotic fluid and cerebrospinal fluid. Other fluids which may be analyzed according to the present invention include water, surface and ground foods and beverages, diagnostic and pharmaceutical compositions, industrial compositions, and other fluids containing or suspected of containing analytes of interest.

Any desired analyte which is present in a fluid sample can be analyzed with the device of the present invention by using the appropriate protocol. The analytes may be haptens or antigens, and include naturally-occurring compounds, synthetic compounds, or combinations thereof. The compounds may vary from methanol to high molecular weight proteins comprising a plurality of subunits. The compounds may be monomeric or polymeric. The assay devices of the present invention can be used to assay for a variety of commonly detected substances, including cholesterol, thyroxine, theophylline, glucose, albumin, ketones, bilirubin, occult blood, nitrite, urobilinogen, hydrogen ion concentration, uric acid, and the like. An extensive list of said analytes is provided in U.S. Pat. No. 4,261,968, which disclosure is incorporated herein by reference.

Categories of analytes of particular interest are those analytes involving both naturally occurring and synthetic drugs, particularly those used for treating chronic conditions, such as valproate, theophylline, barbiturates, etc., drugs of abuse, and the like. Other compounds of interest are those which are naturally occurring, particularly physiologically active compounds, such as hormones, growth factors, colony stimulating factors, interferons, surface membrane proteins, viral proteins, animal proteins, antibodies, enzymes, etc., both proteinaceous and non-proteinaceous. The conjugates which are prepared may be prepared in conventional ways, and will vary with the particular component which interacts with the enzyme and the nature of the analyte.

Specific examples of analytes which serve as a substrate for an enzyme, resulting in a product which can further react with another compound to produce a detectable product, particularly a visually colored product, include galactose, glucose, cholesterol, urea, nicotinamide adenine dinucleotide, riboflavin, uric acid, and the like.

Analytical Device and Methods

Figure 6:
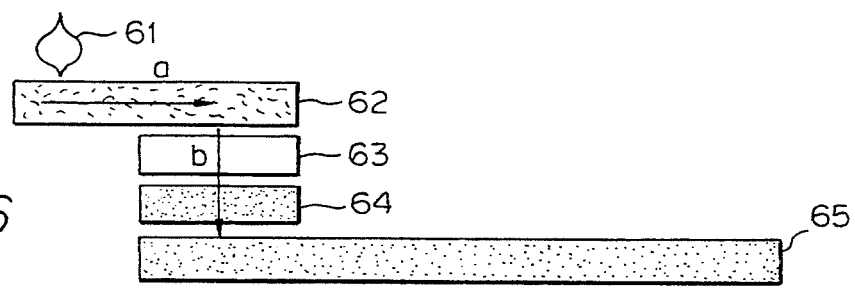
FIG. 6 illustrates an assay device incorporating a flow-delay layer.

One embodiment of the assay device of the present invention is illustrated in FIG. 6. When a whole blood sample 61 contacts the device 66, the sample 61 first contacts the absorbent pad 62. From the absorbent pad, the sample flows through to the reagent layer 63. The flow delay layer 64 is below the reagent layer so that the sample has time to incubate with the reagent(s) in the reagent layer. After a predetermined period of time, the flow delay layer opens, and the sample flows through to the measurement zone 65.

Other embodiments may be obtained by varying the reagents, measurement zone, and flow delay means and methods, etc., as described below.

Reagents

The reagents used in assay devices according to the present invention are any reagents that react with the analyte of interest to produce a product which can give a detectable signal. For example, galactose, glucose or other saccharides, cholesterol, urea, nicotinamide adenine dinucleotide, riboflavin, compounds which result in the reduction or oxidation of co-factors, such as NAD or NADP, can be assayed with conventional reagents which produce known products.

For those analytes which result in the production of hydrogen peroxide, namely, those compounds which are associated with oxidases, the resulting hydrogen peroxide may react in the presence of a peroxidase such as horseradish peroxidase, with a wide variety of horseradish peroxidase substrates. These substrates include o-chlorophenol benzidine, tetramethylbenzidine, dimethylaniline in conjunction with 3-methyl-2-benzothiazolinone hydrazone (MBTH), dicarboxidine, o-dianisidine, 4-chloro-1-naphthol, and the like. The compounds which are bound to the assay measurement zone may react by themselves with the reagent-analyte product or in conjunction with a component in the transport medium.

Where various reductants are produced, such as NADH, FMNH, etc., compounds which may be bound in the measurement region may include methylene blue, N-methyl phenazine methosulfate, ferrocene, ferridoxin, cytochrome c, triphenyltetrazolium, etc., preferably where the reduced compound is colored.

Another format involves analytes which are not substrates of enzymes which produce a product which can be used to produce a detectable signal by reacting with another substance. These analytes can be employed in a variety of ways where the analyte or analyte analog is joined to another compound which serves to modulate enzyme activity. For example, co-enzyme conjugates can be prepared where the co-enzyme conjugate competes with the analyte for antibody to the analyte. The antibody bound conjugate will be unable to bind to the enzyme and no reaction will occur. Free co-enzyme conjugate will be able to bind and allow for a single reaction in the absence of a regeneration system.

The device of the present invention can be used to monitor any solution comprising a first compound which by itself or by enzymatic transformation reacts with another compound to produce a signal resulting in a detectable boundary in the measurement zone. Therefore, any methodology which provides such a first compound can be monitored. By using a plurality of determinations, rate measurements can be made, where the reaction does not continue in a significant manner once transferred to the sample pad. Alternatively, the reaction is terminated so that no further reaction occurs, and then this solution is used for impregnating the sample pad.

For immunological reactions, the assay reagents necessary for performing a binding assay are incorporated into the reagent layer or layers. The specific binding assay determination of analyte from a fluid sample typically involves binding among the analyte, a reversibly immobilized labelled reagent, and a binding partner of the analyte, or the analyte or binding analog thereof. The labelled reagent comprises the analyte of binding analog thereof, or a binding partner of the analyte, respectively, depending upon the nature of the immobilized reagent, labelled with a detectable chemical group having a detectable chemical or physical property.

For many assays, a second reagent or other assay reagents which are similarly capable of interacting with the first reagent to provide a detectable signal, are incorporated into a detection layer in an insolubilized form according to conventional methods well known in the art. Where an assay reaction or interaction involves a labelled reagent comprising a chemical group having a detectable chemical property, such as an enzyme, the interaction of the enzyme with a second reagent, such as a substrate for the enzyme, incorporated into a measurement zone, results in the generation of a reaction product which either inherently provides a detectable signal or requires further interaction with another substance or other substances to provide a detectable signal, depending upon the nature of the label of the labelled reagent and the second reagent.

Similarly, where the labelled reagent comprises a chemical group having a detectable physical property, this labelled reagent can further include a binding site for the second reagent which comprises a binding substance or binding counterpart for the binding site of the labelled reagent. Accordingly, selection of an appropriate binding substance for immobilization in the measurement zone layer necessarily depends upon the selective recognition of the binding site by the binding substance. In one example, the labelled reagent comprises a ligand moiety which forms a specific binding pair with the binding substance. In particular, preferred representative binding pairs for the ligand moiety and the binding substance include such binding pairs as haptens and antibodies, or fragments thereof, to the haptens; biotin and avidin; carbohydrates and lectins; and antibody, or fragment thereof, having an intact binding site for Protein A and Protein A. Additional binding pairs include complementary single stranded oligonucleotide sequences; effector molecules and receptor pairs; prosthetic groups and apoproteins; enzyme cofactors and enzymes; polymeric acids and bases; dyes and protein binders; peptides and specific protein binders (e.g., ribonuclease, S-peptide and ribonuclease S protein); enzyme inhibitors (reversible and irreversible), enzymes, and the like.

The labelled reagent can be selectively immobilized in the measurement zone by binding to an adsorbent material for the labelled reagent, such as an ion exchange material, which acts as the binding substance, which is immobilized in the detection layer. Other materials may also be employed as a binding substance for the first or labelled reagent provided.

Measurement Zone

After the fluid sample has incubated with the reagents for an appropriate predetermined period of time, which time depends upon the particular reaction and is well known to those skilled in the art, the fluid sample flows through the reagent zone to the measurement zone. In the measurement zone, the sample which has reacted with reagents in the reagent zone to form the appropriate products contacts a signal producing system.

The signal producing system may have one or more components which, in the presence of the product produced in the reagent layer, produce a detectable signal. The signal producing system includes all of the reagents required to produce a measurable signal, as well as a developer. The developer may include substrates, coenzymes, enhancers, second enzymes, activators, cofactors, inhibitors, scavengers, metal ions, specific binding substances required for binding to signal generating substances, and the like. The components of the signal producing system may be bound to the measurement zone such as coenzymes, substances that react with enzymatic products, other enzymes and catalysts, and the like.

The signal producing system provides a signal detectable by external means, normally by measurement of electromagnetic radiation, desirably by visual examination. Most commonly, the signal producing system includes a chromophoric substrate and an enzyme, where the chromophoric substrates are enzymatically converted to dyes which absorb light in the ultraviolet or visible region, phosphors or fluorophores. The signal producing system preferably provides a detectable signal related to the amount of analyte originally present in the sample.

Many of the commonly used assays for substances present in biological fluids, such as cholesterol, lipoproteins, glucose, uric acid and the like, are assayed using enzymes which involve the production of hydrogen peroxide and the use of the hydrogen peroxide to oxidize a dye precursor to a dye. Particular combinations include saccharide oxidases, such as glucose and galactose oxidase, or heterocyclic oxidase, such as uricase and xanthine oxidase, coupled with an enzyme which employs the hydrogen peroxide to oxidize a dye precursor, e.g., a peroxidase such as horseradish peroxidase, lactoperoxidase, and microperoxidase. Additional enzyme combinations are well known to those skilled in the art of clinical assays.

When a single enzyme is used as a label, other enzymes may find use such as hydrolases, transferases, and oxidoreductases, preferably hydrolases such as alkaline phosphatase and beta-galactosidase. Alternatively, luciferases may be used, such as firefly luciferase and bacterial luciferase.

The product of the enzyme reaction is usually a dye or fluorescer. These dyes or fluorescers are chosen for their sensitivity to the reaction product as well as for their sensitivity as required for each assay.

Flow Delay Means

The flow delay means of the present invention comprises a coatable, impregnatable or couplable material which has been coated, impregnated or coupled with a sizing material, i.e., substance which retains fluid for a predetermined period of time, and then permits substantially all of the fluid to flow through the material. The time period that the sample is retained on the flow delay means can be controlled by selecting the sizing material and the amount of this sizing material used to coat or impregnate the material. This coating or impregnating process is also referred to as "sizing" the substrate.

The flow delay means of the present invention can take a variety of forms. For example, a fibrous or absorbent material is impregnated with an alkyl ketene dimer or a fatty acid chloride, or coated with a fluorocarbon resin. Some of the mechanisms which promote flow delay are described below.

FIG. 1 shows how alkyl ketene dimers react with cellulose. At the beginning of the reaction scheme, a fatty acid chloride is reacted with triethylamine and triethylamine hydrochloride to form an alkyl ketene (not isolated), which dimerizes to form the alkyl ketene dimer. When this alkyl ketene dimer is reacted with cellulose (paper fibers), the alkyl ketene dimer reacts with the hydroxyl group at the end of the cellulose molecule to form a sized paper.

In the present invention, however, materials in addition to cellulose are treated. For example, glass fibers or polyamide or other synthetic fibers are treated with the alkyl ketene dimers in a similar manner. The alkyl ketene dimers can be applied from solution (such as from dichloromethane, ethyl acetate, and the like) or from an aqueous emulsion. Alternatively, the precursors to alkyl ketene dimers, the fatty acid chlorides, can be attached directly to or merely deposited onto the substrate to be treated.

Sizing of the fibrous or absorbent material works because long, hydrophobic fatty acid chains, when deposited onto a relatively hydrophilic surface such as paper or glass, spread out and create a moisture-impervious shield on the surface. This shield can be thought of as an umbrella.

Figure 7:
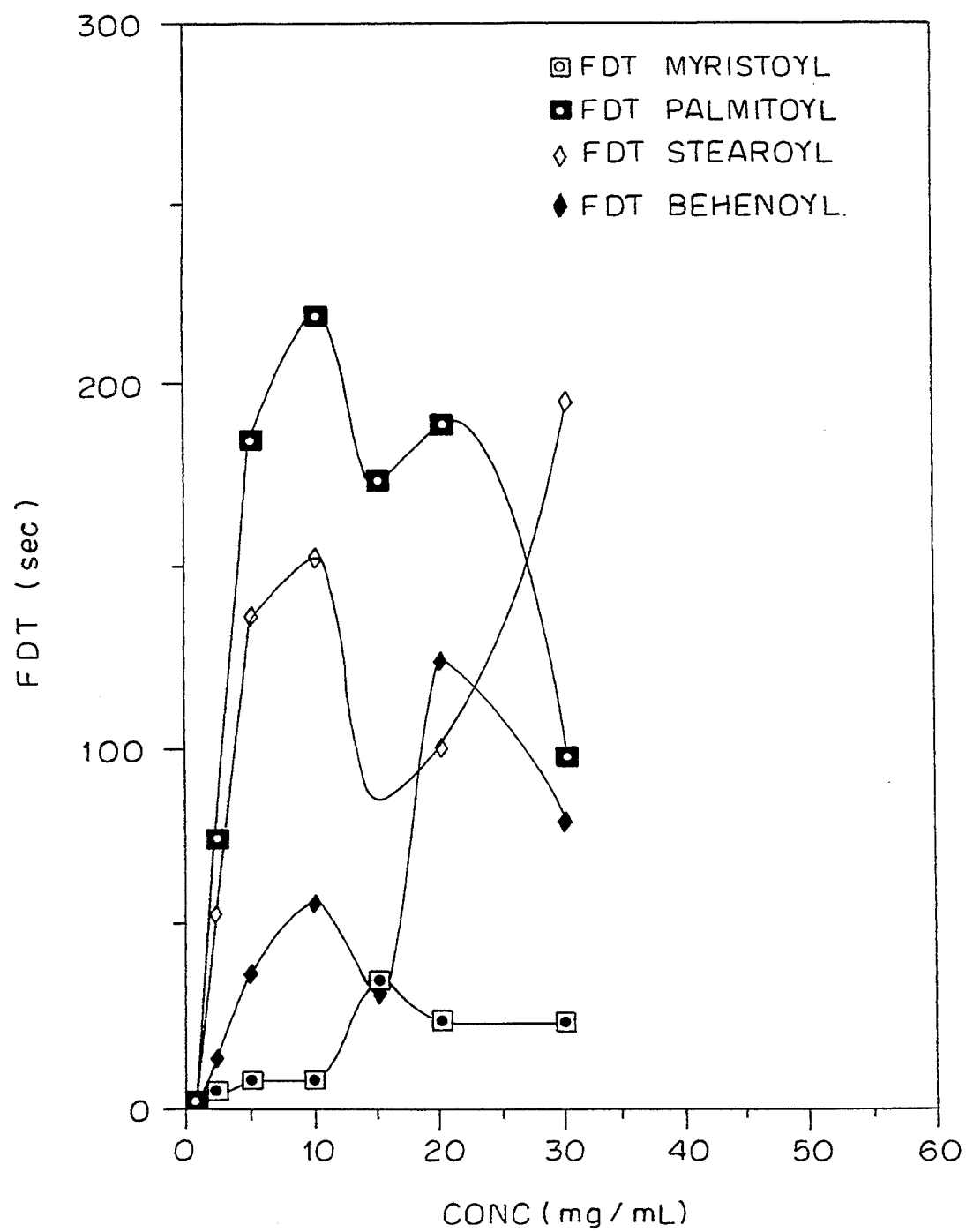
FIG. 7 illustrates flow delay times for a variety of saturated alkyl ketene dimers.
Figure 8:
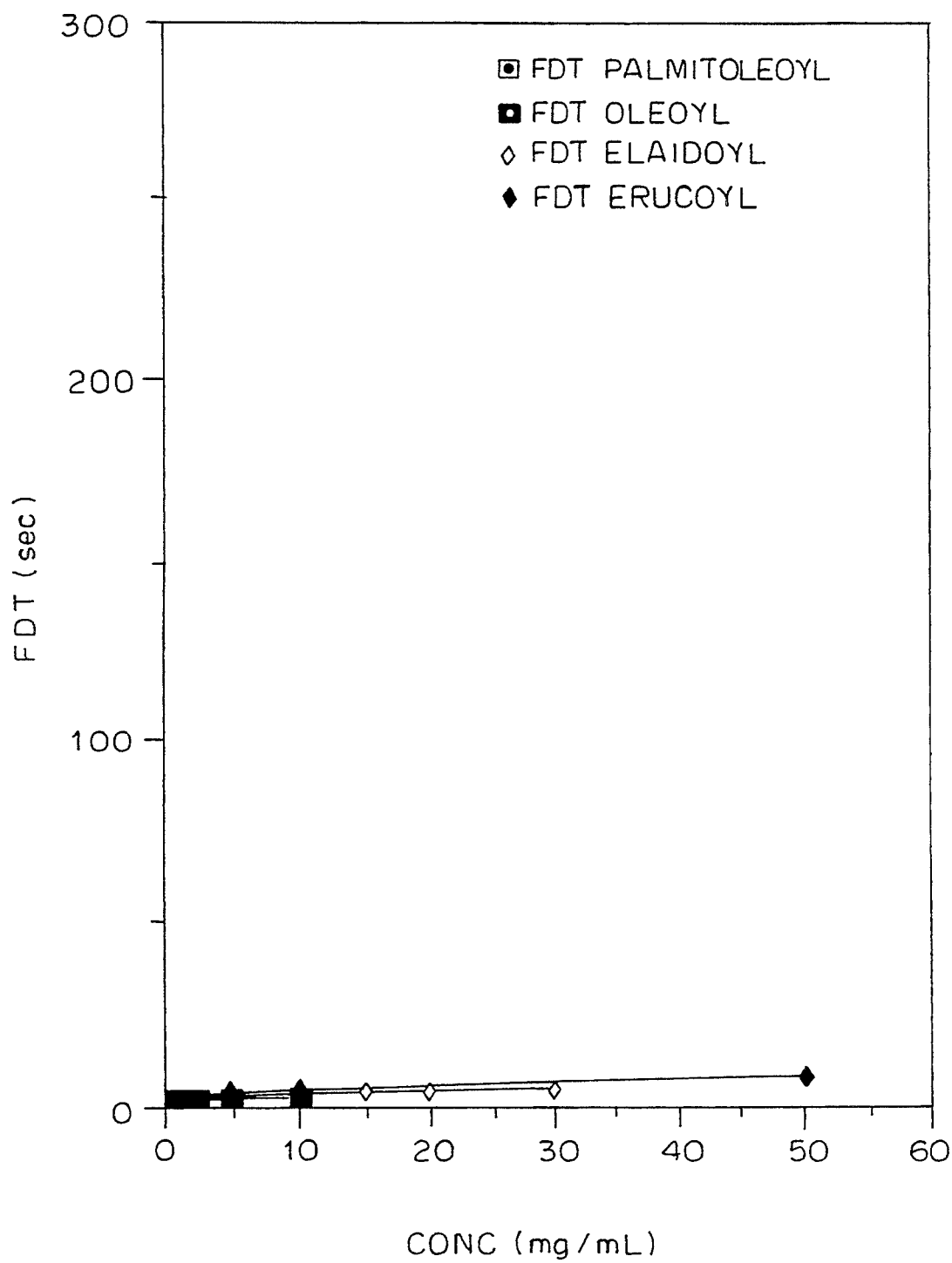
FIG. 8 illustrates flow delay times for monounsaturated alkyl ketene dimers.

A wide range of alkyl ketene dimers have been found to provide valuable flow delay for fluid samples. Among these alkyl ketene dimers are palmitoyl ketene dimer ($C_{16}$), saturated fatty acid ketene dimers such as stearoyl ($C_{18}$), behenoyl ($C_{22}$), and myristoyl ($C_{14}$). Accordingly, alkyl ketene dimers of fatty acids having at least 14 carbon atoms, and up to about 30 carbon atoms, are preferred for the present invention. Lower molecular weight alkyl ketene dimers, such as capryloyl ($C_8$), lauroyl ($C_{12}$), do not provide the degree of flow delay necessary for use in assays of fluid samples. Moreover, fatty acid ketene dimers of equal chain length but containing at least one site of unsaturation do not provide the degree of flow delay required, as shown in FIGS. 7 and 8 and Table 1. There is no upper limit to the number of carbon atoms in the fatty acid precursors of the alkyl ketene dimers. The only limit to the number of carbon atoms in the dimers is the ease of coating or impregnating substrates with the dimers.

The fatty acid chlorides for use in the present invention as sizing materials are saturated fatty acid chlorides such as palmitoyl chloride ($C_{16}$), stearoyl chloride ($C_{18}$), benenoyl chloride ($C_{22}$) and myristoyl chloride ($C_{14}$). As with the alkyl ketene dimers there is no upper limit to the number of carbon atoms in the fatty acid chloride. The only limit to the number of carbon atoms in the fatty acid chloride is the ease of coating or impregnating substrates with the fatty acid chlorides.

TABLE 1

| Type sizing | HC; satn | Conc. (mg/mL) | mM | Average flow delay time (sec.) |
|---|---|---|---|---|
| UNSATURATED | | | | |
| Palmitoleoyl | C16; cis-9 | 10.00 | 21.15 | 2 |
| Palmitoleoyl | | 5.00 | 10.58 | 2 |
| Palmitoleoyl | | 2.50 | 5.29 | 2 |
| Palmitoleoyl | | 1.00 | 2.12 | 2 |
| Palmitoleoyl | | 0.50 | 1.06 | 2 |
| Oleoyl | C18; cis-9 | 10.00 | 18.91 | 2 |
| Oleoyl | | 5.00 | 9.45 | 2 |
| Oleoyl | | 2.50 | 4.73 | 2 |
| Oleoyl | | 1.00 | 1.89 | 2 |
| Oleoyl | | 0.50 | 0.95 | 2 |
| Erucoyl | C22; cis-13 | 50.00 | 77.98 | 8 |
| Erucoyl | | 10.00 | 15.60 | 5 |
| Erucoyl | | 5.00 | 7.80 | 4 |
| Erucoyl | | 2.50 | 3.90 | 2 |
| Erucoyl | | 1.00 | 1.56 | 2 |
| Erucoyl | | 0.50 | 0.78 | 2 |
| Elaidoyl | C18; trans-9 | 30.00 | 99.67 | 5 |
| Elaidoyl | | 20.00 | 66.45 | 4 |
| Elaidoyl | | 15.00 | 49.83 | 4 |
| Elaidoyl | | 10.00 | 33.22 | 3 |
| Elaidoyl | | 5.00 | 16.61 | 3 |
| Elaidoyl | | 2.50 | 8.31 | 2 |
| Elaidoyl | | 1.00 | 3.32 | 2 |
| SATURATED | | | | |
| Myristoyl | C14; satd | 30.00 | 71.31 | 23 |
| Myristoyl | | 20.00 | 47.54 | 24 |
| Myristoyl | | 15.00 | 35.65 | 35 |
| Myristoyl | | 10.00 | 23.77 | 8 |
| Myristoyl | | 5.00 | 11.88 | 8 |
| Myristoyl | | 2.50 | 5.94 | 5 |
| Myristoyl | | 1.00 | 2.38 | 2 |

TABLE 1-continued

| Type sizing | HC; satn | Conc. (mg/mL) | mM | Average flow delay time (sec.) |
|---|---|---|---|---|
| Palmitoyl | C16: satd | 30.00 | 62.92 | 97 |
| Palmitoyl | | 20.00 | 41.94 | 188 |
| Palmitoyl | | 15.00 | 31.46 | 173 |
| Palmitoyl | | 10.00 | 20.97 | 218 |
| Palmitoyl | | 5.00 | 10.49 | 184 |
| Palmitoyl | | 2.50 | 5.24 | 73 |
| Palmitoyl | | 1.00 | 2.10 | 2 |
| Stearoyl | C18; satd | 30.00 | 56.29 | 195 |
| Stearoyl | | 20.00 | 37.53 | 100 |
| Stearoyl | | 15.00 | 28.15 | 84 |
| Stearoyl | | 10.00 | 18.76 | 152 |
| Stearoyl | | 5.00 | 9.38 | 136 |
| Stearoyl | | 2.50 | 4.69 | 53 |
| Stearoyl | | 1.00 | 1.88 | 2 |
| Behenoyl | C22; satd | 30.00 | 46.50 | 78 |
| Behenoyl | | 20.00 | 31.00 | 123 |
| Behenoyl | | 15.00 | 23.25 | 31 |
| Behenoyl | | 10.00 | 15.50 | 56 |
| Behenoyl | | 5.00 | 7.75 | 37 |
| Behenoyl | | 2.50 | 3.88 | 14 |
| Behenoyl | | 1.00 | 1.55 | 2 |
| Behenoyl | | 0.50 | 0.78 | 2 |

Figure 2:
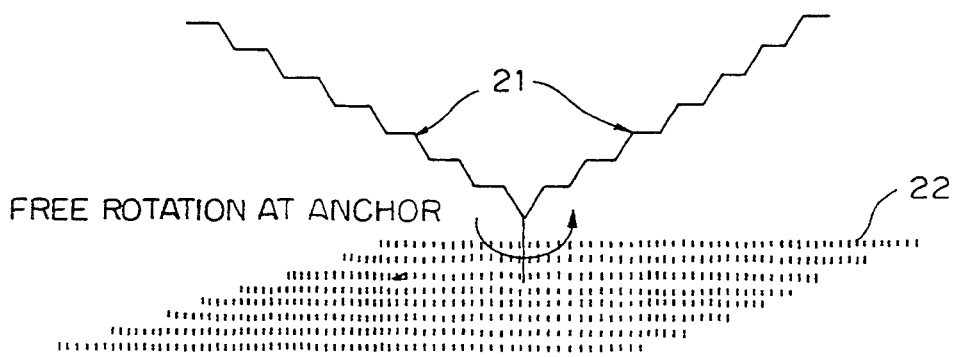
FIG. 2 shows how alkyl ketene dimer sizes a matrix.

FIG. 2 shows the fatty chains 21 of an alkyl ketene dimer sweeping the surface of the matrix 22 which has been impregnated therewith. In this case, the degree of sizing is determined by the density of the fatty chains on the surface of the substrate.

Fluorocarbon resins create a similar environment. However, fluorocarbon resins do not usually rely upon an anchoring site for attachment. Instead, these resins bloom to the surface of the material onto which they are deposited, where they remain to create a moisture-impervious shield. Fluorocarbon resin sizes have been used extensively for treating apparel fabrics, upholstery fabrics, and carpeting to provide moisture- and stain-resistance. In this case, the absorption of fluids onto the surface treated is slowed by the sizing agent. After a given retention time, the fluid flows into the adjoining bibulous layer, which absorbs the fluid very quickly. This sizing, then, acts in the same way as a valve, in that the fluid is kept out for a certain period of time, and then is all permitted to flow into the adjoining layer.

The fluorocarbon resins that can be used in the present invention are those which are conventionally used for treating fabric (both apparel and upholstery) for water-resistance. The formulations specifically used in the present inventions, FX-327 and FC-3537, are trade secret formulations of the 3M Company; it is known that the primary ingredient in these formulations is fluoropolymers. These fluoropolymers can be substantially completely hydrophobic or the fluoropolymers can have both hydrophobic and hydrophilic moieties. Further characteristics of these materials can be obtained by appropriate physical and chemical assays known to those skilled in the art, including but not limited to average molecular weight of the fluorocarbon resins, degree of fluorination and the like.

Fluoromonomers were found to be unacceptable as flow delay treatments. Several perfluorinated monomers were coated onto glass fiber pads, but these compounds did not demonstrate any sizing capability. Thus, fluoropolymers rather than monomers are required for the type of sizing needed to provide a valve-like action.

The fluoropolymers used for sizing do not dissolve in the fluid stream, unlike soluble polymers such as polyvinyl pyrrolidone and polyethylene glycol, which do dissolve in the fluid stream after a predetermined time.

Although the fluoropolymers delay flow through a temporary barrier layer, there is no concomitant slowdown in overall flow time in the device below a dosage of about 0.008 μg/pad of fluorocarbon size. Table 4 and FIG. 3 illustrate this feature.

Figure 3:
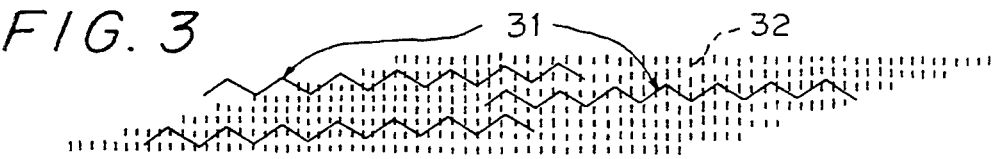
FIG. 3 shows sizing of a matrix with a fluorocarbon resin.

FIG. 3 illustrates how fluorocarbon resins provide a water-resistant shield to a substrate. The fluorocarbon resins 31 do not chemically attach functional groups on the surface of the matrix 32, but instead merely bloom to the surface of the matrix and reside there due to their hydrophobic nature.

There are commercial compounds which contain alternating hydrophilic and hydrophobic regions or domains. One example of this type of compound is Du-Pont ZONYL, which has a hydrophilic structure and a fluorinated hydrophobic tail. The hydrophilic domains are "anchored" physicochemically rather than covalently in the hydrophilic matrix, while the hydrophobic domains remain at the surface. This anchoring comes from the alternating domains seeking regions which are compatible: the philic portions assemble in the philic glass-fiber or paper milieu. The phobic portions, which do not find compatible surroundings, exit to the surface ("bloom") and remain at the surface.

Figure 4:
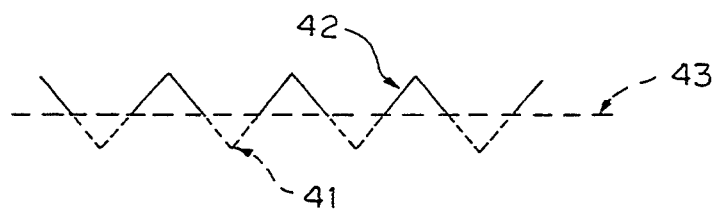
FIG. 4 shows how compounds having both hydrophilic and hydrophobic domains coat a matrix surface.

FIG. 4 illustrates how compounds with both hydrophilic 41 and hydrophobic 42 domains reside comfortably and securely at the matrix surface 43.

Other candidate flow materials may be evaluated for suitability by applying them to a substrate and measuring flow delay and total flow time before and after application (see Examples).

Figure 5:
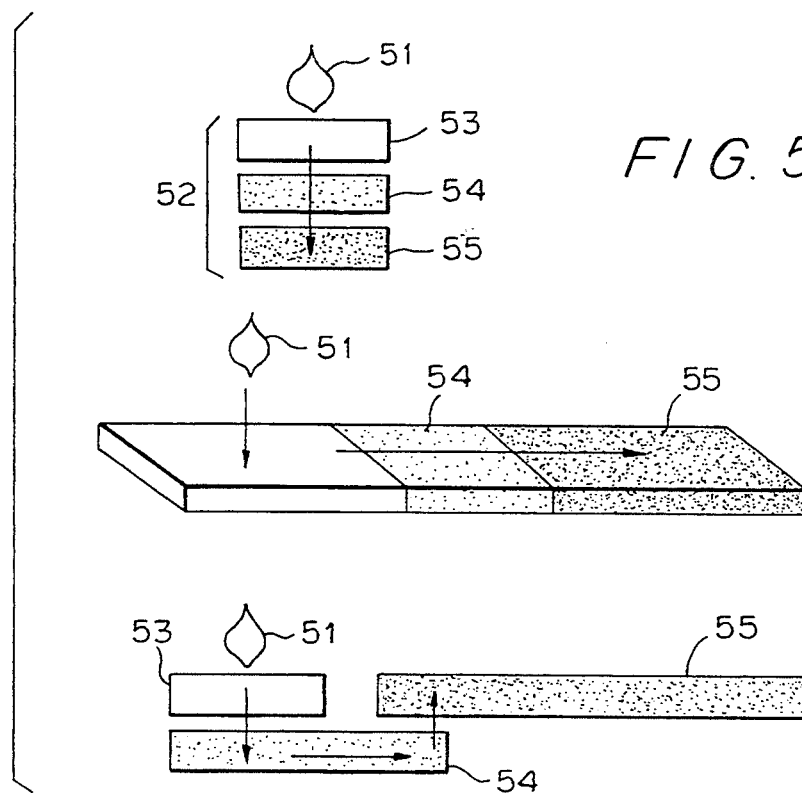
FIG. 5 shows configuration for flow delay pads for assay devices.

FIG. 5 illustrates representative configurations of flow delay means according to the present invention. As the sample fluid 51 reaches the reaction zone 52, and contacts the reagent layer 53, the chemical reaction starts. The flow delay pad 54 stops the flow of the fluid for a pre-determined incubation period. After this incubation period, the fluid is permitted to flow to the post-reaction zone 55.

FIG. 6 illustrates another configuration for an assay device using the flow delay layer of the present invention. A sample 61 first contacts and absorbent pad 62 which draws the sample into the assay device. The sample then contacts the reagent layer 63 and is retained there for a predetermined time by the flow delay layer. After the predetermined time, the flow delay layer permits the sample to flow through to the measurement zone 65.

The pad forming the flow-delay layer is prepared by optionally first dosing it with lactose, followed by drying. The lactose-treated pads are then dosed with an ethyl acetate solution of palmitoyl ketene dimer, either by micropipet, IVEK pump, syringe pump, dropping, or other compatible method. The method of dosing is not critical to the formation of the pads. The pads are then dried in an oven at 100° C. for about 30 minutes to develop the size.

The range of sizing material per pad can range from about 0.0001 microgram to about 100 micrograms per pad, although more or less of the sizing material can be added to the pad if different flow times are desired. One example of flow control means is about 5.5 microliter of a 5 mg/mL ethyl acetate solution of palmitoyl ketene dimer on each pad (0.2"×0.3"), i.e., 27.5 micrograms of palmitoyl ketene dimer per pad.

The amount of flow control means is varied depending upon how long a flow delay time is required to give an accurate test. For example, while a two minute flow delay is sufficient for total cholesterol, HDL requires a longer flow delay time, of approximately 3.5 minutes. Using the system of the present invention, the amount of sizing agent is varied so as to vary the amount of flow delay desired.

For purposes of flow delay, the pads can be made from materials such as glass or synthetic fibers. The pads can be woven or nonwoven. The fibers from which the pads are made are preferably hydrophilic, either by the nature of the fibers themselves or by post-treatment of the fibers. The fiber size is not material.

The mesh or pore size of the pad can average about 200 microns, with a preferred range being from about 20 to about 500 microns.

Methods used for Flow Delay

Flow delay can be effected in assay devices by a variety of means. As noted previously, many workers have tried means for delaying flow for a number of different purposes. Some of these means include dissolution, swelling, chemical reaction, and sizing. Experiments were conducted to compare the various flow delay techniques.

Dissolution

Support matrices were impregnated with water soluble compounds such as polyethylene glycol or sugars (sucrose, mannitol, sorbitol, and the like) to form a flow delay pad. The fluid was stopped upon reaching the flow delay pad, and the time required to dissolve the compounds so that the fluid can penetrate and continue flowing through the pad is the delay mechanism. Many of these trials gave 5–90 second flow delays, but the delay times were unreliable. Moreover, the overall flow rate slowed due to the increase of viscosity of the fluid from dissolving the flow delay compounds. These data are shown in Table 2. Another problem associated with dissolution is that the sample is contaminated by an extraneous material.

Swelling

Compounds which swell upon contact with water can be used to coat a flow delay pad. Examples of such compounds include shellac gum. Although these swelling compounds were found to be effective for delaying flow, the swollen barrier formed by the swollen compound restricted the total flow rate excessively. Restricting the flow rate poses the danger that insufficient sample will flow through the pad to effect the remaining reactions which cause the detectable signal, thus providing an invalid assay.

Chemical reaction

Chemical reactions, such as a proteolytic enzyme acting on a proteinaceous source, can be used to delay flow through a pad. Gelatins were coated onto pads to provide a flow delay barrier. Protease in the reagent zone slowly broke down the gelatin film, opening the barrier for fluid flow to continue. Unfortunately, the flow delay pads prepared in this manner gave very inconsistent delay times. As with dissolution, this technique introduced extraneous matter into the sample.

Sizing

Surprisingly, application of the sizing materials of the present invention onto flow delay pads provided the required characteristics of flow delay for a predetermined discrete period of time, highly reproducible flow delay times, and no effect on viscosity of the fluid.

In all of the above cases, the pad used was a glass fiber pad a glass fiber filter with a mean pore size of 1.2 microns and a thickness of about 700 microns. These pads were pretreated with lactose as described above.

The sizing materials of the present invention, unlike materials which attempt to delay flow by dissolution, swelling or chemical reaction, provide reproducibility of results without affecting the viscosity or chemical composition of the sample. There is no diffusion of the detection signal produced by the sample when the sizing materials of the present invention are used to delay the flow.

TABLE 2

Flow control by various chemical coatings

| Material | Flow delay mm ss | Total flow time min | Comments |
|---|---|---|---|
| Sucrose | 1.4–12.00 | 16–32 | very inconsistent flow |
| Mannitol | 1.3–2.30 | 12 | fuzzy endpoints at high concentration |
| Sorbitol | 1.00 | 11–25 | diffuse endpoints |
| Lactose | 1.00 | 9–10 | increasing conc. did not increase delay; no effect on total flow time |
| PEG | <0.30 | 16–27 | dam did not hold; endpoints not sharp; dam does not totally dissolve; at high conc., poor penetration of dam and slow color development |
| Shellac gum | 1.30 | 7 | increasing conc. did not increase delay |
| Gelatin | 2.30 | 19–25 | inconsistent retention times as pads got drier; cracked and lost flow delay ability; increased flow times |
| Gelatin + protease | 1.30 | 30 | less delay with protease |

It should be understood that the flow delay means of the present invention may be, if desired, combined with other methods of flow delay.

Application of Sizing to Pads

The substrates to be used as flow delay pads can be treated in two principal ways:

(1) by reacting functional groups on the sizing compound(s) with functional groups on the surface of the substrate; or (2) by imbibing a sizing composition onto the material, such as from a dilute solution, either by dipping the material into the solution or by pipetting discrete aliquots of the solution onto the substrate, followed by evaporating the carrier solvent.

However, the present invention is not limited to any particular method of applying the flow delay material to the substrate.

EXAMPLE 1

Alkyl Ketene Dimer Sizing

Preparation of alkyl ketene dimer sizing composition

For this example, the alkyl ketene dimer used was palmitoyl ($C_{16}$) ketene dimer, a typical fatty acid ketene dimer. The ketene dimer was prepared by dissolving 27.5 grams palmitoyl chloride in 200 mL ethyl acetate in a 500 mL Erlenmeyer flask. Then, 10.1 grams triethylamine was dissolved in 50 mL ethyl acetate and placed into an addition funnel. The solution of triethylamine was dripped slowly into the stirring acid chloride solution. A white precipitate began to form almost immediately; this white precipitate was triethylamine hydrochloride. The solution was stirred for one hour after all of the triethylamine was added. The triethylamine hydrochloride was filtered out of the solution, and the filtrate, a clear, golden-yellow solution, was evaporated under reduced pressure to yield a light yellow, waxy solid, palmitoyl ketene dimer. The yield was virtually quantitative.

Application of alkyl ketene dimer size onto glass fiber pads by imbibition

A stock solution was prepared by dissolving one gram of palmitoyl ketene dimer in 25 mL ethyl acetate. This stock solution was diluted to appropriate levels, i.e., to a level that permits mechanical dispensing of the solution onto pads in a precise manner. Given pads of a size approximately 0.2"×0.3", no more than 6 microliters of solution should be applied to each pad so that the solution does not seep beyond the confines of the pad itself. To obtain 25 micrograms of size on the pad, the stock solution is diluted to a level such that 4 to 6 microliters deposit 25 micrograms of sizing material. The actual concentration of the dosing solution is immaterial as long as the solution can readily be mechanically dispensed onto the pad without seeping out of the pad; the amount of sizing applied, i.e., grams of sizing per pad, is the critical amount in effecting flow delay.

One gram of palmitoyl ketene dimer was dissolved in 25 mL ethyl acetate. This stock solution was diluted to appropriate levels to provide flow delay, and six microliter aliquots of a chosen dilution were applied to precut glass fiber filter pads which had been pre-treated with lactose. The pads were cut from Ahlstronm Filtration grade 100 glass-fiber sheets. The pads were pretreated with lactose by dosing each pad with a 36.4 mg/mL solution of d-lactose in water so that the final dosage was 200 micrograms lactose per pad. The pads were dried in a 100° C. oven for 30 minutes and cooled in a desiccated atmosphere. The pads were installed in a disposable assay device for testing.

Application of alkyl ketene dimer size by reaction with paper

As shown in FIG. 1, alkyl ketene dimer sizes readily react with the hydroxy groups on cellulose. Consequently, paper is readily impregnated with alkyl ketene dimers by coating the paper with a solution of the alkyl ketene dimer, evaporating the solvent, and curing the sizing with heat, such as for thirty minutes at 100° C. The sized and cured paper was then subjected to extensive extraction with solvent such as dichloromethane or ethyl acetate. This extraction is readily accomplished by soaking the paper in the solvent, or by Soxhlet extraction. This is a procedure conventionally used in the paper industry to show that size is chemically anchored to paper. Because none of the alkyl ketene dimer was extracted from the paper, it was concluded that the sizing molecule was covalently attached to the surface of the paper.

Flow Delay by Alkyl Ketene Dimer

Alkyl ketene dimer was applied to glass fiber pads as described in Example 1 to yield pads having different amounts of alkyl ketene dimer applied thereto. After the pads had been prepared, they were combined with an assay device as shown in FIG. 6, and a sample of whole blood was applied thereto.

Table 3 below shows that an increase in the amount of sizing added to the flow-delay pad results in an increase in the flow delay time without a concomitant increase in the total flow time.

TABLE 3

Flow control by palmitoyl ketene dimer.

| Concentration | Flow delay time mm.ss | Total flow time mm |
|---|---|---|
| 11 μg | 1.00 | 12 |
| 20 μg | 1.30 | 11 |
| 30 μg | 2.30 | 12 |
| 40 μg | 2.30 | 12 |
| 60 μg | 2.50 | 12 |

"Flow delay time" is the time interval from the absorption of whole blood into the absorbent pad, its flow through the reagent layer, and its incubation at the reagent layer, to the point when it is first detected at the measurement zone. The "Total flow time" is the time required for the sample to flow through the measurement zone.

EXAMPLE 2

Fatty Acid Chloride Sizing

Application of fatty acid chloride size by reaction with paper

A 5.5 cm. Whatman #1 filter paper disk was soaked for 15 minutes in a 15% solution of NaOH. The paper was transferred to a Büchner funnel and sucked dry. The paper disk was then washed with 100 mL each of dioxane and acetone to remove water, and dried in the air. The disk was cut into eight pieces.

A solution of palmitoyl chloride was prepared by dissolving 0.5 g palmitoyl chloride in 5 mL dichloromethane.

A ⅛ section of the NaOH-treated filter paper was soaked for 15 minutes in the palmitoyl chloride solution, then washed thoroughly with dichloromethane to remove any unreacted palmitoyl chloride. The amount of fatty sizing material attached to the paper is easily adjusted by adjusting the concentration of the palmitoyl chloride solution. The protonated form of the paper can be regenerated by soaking in a dilute acid solution.

Alternatively, fatty acid chloride was coated directly onto a paper from a dilute solution in dichloromethane. Although this material developed sizing properties, it required a longer time to develop these sizing properties. It was postulated that the sizing properties required longer to develop because the reaction of acid chloride with available hydroxy groups on the paper is slower without the presence of the additional base on the protonated paper.

EXAMPLE 3

Fluorocarbon Resin Sizing

Preparation of fluorocarbon size.

Small amounts of fluoroaliphatic resins were applied to substrates such as paper or glass fiber pads. The levels of fluoroaliphatic resin useful in flow delay pads were in the range of thousandths of a microgram, e.g., from 0.0005 microgram to about 0.01 microgram per pad. The pad dimensions for this amount of resins were 0.2 inch×0.3 inch. Each pad weighed approximately 1 mg. Thus, dosage was calculated either as the amount of sizing agent per area of pad or amount of sizing agent per gram of pad material. For fluoroaliphatic resins, the ranges of resin used were from about 0.005 microgram/$in^2$ to about 0.2 microgram/$in^2$. The fluorocarbons are readily obtained in either aerosol or liquid form as products for treating fabric or carpets, such as 3M FX-327, FC-3537, Scotchgard® fabric treatment spray, and similar formulations. To apply the fluorocarbon resin from an aerosol, the product was sprayed directly onto the substrate, or was first diluted with an appropriate solvent. Liquid fluorocarbon resins were diluted to provide from about 0.005 microgram to about 0.001 microgram of fluorocarbon resin per pad. Suitable solvents are ethyl acetate, chloroform, dichloromethane, hexanes, etc, depending upon the sizing agent's particular solubility characteristics. The method for dilution and application by imbibition for fluorocarbon sizes was identical to that used for alkyl ketene dimer sizes.

Example 1 was repeated using a pad impregnated with a fluorocarbon resin as described above for the flow delay material.

Table 4 shows that, for fluorocarbon resins, there is a useful concentration of resin per pad, generally up to about 0.008 μg resin per pad. Beyond that concentration of fluorocarbon resin per pad, there is a rapid increase in flow delay time, and total flow time, for small increases in dosage of fluorocarbon sizing.

TABLE 4

Flow control by fluorocarbon resin.

| Concentration | Flow delay time mm.ss | Total flow time mm |
|---|---|---|
| 0.0014 μg | 1.00 | 10.30 |
| 0.0034 μg | 1.15 | 10.25 |
| 0.007 μg | 2.30 | 14.00 |
| 0.014 μg | >30.00 | >60.00 |

EXAMPLE 4

Other sizing materials

Other sizing materials such as fatty ($C_{12}$–$C_{24}$) acids, fatty ($C_{12}$–$C_{24}$) alcohols, alkenyl succinic anhydrides, were applied to the desired pad material from dilute solutions of solvents appropriate to the compound being applied: ethyl acetate, dichloromethane, chloroform, trichloroethylene, acetone, toluene, methanol, ethanol, hexanes, and the like. The dilutions of fatty alcohols, fatty acids and alkenyl succinic anhydrides are comparable to those used for palmitoyl ketene dimer. Although these materials were somewhat effective in delaying flow for a predetermined time, they were not as effective as the materials described above.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed is:

1. A method for delaying flow of a fluid sample through a porous substrate which is part of a flow delay layer of an analytical device comprising a reagent layer, the flow delay layer positioned below said reagent layer and a measurement zone positioned below said flow delay layer wherein the method comprises the step of coating said porous substrate with a flow delay material wherein said flow delay material retains the fluid in the porous substrate for a predetermined period of time and then permits the fluid to flow substantially completely through said porous substrate to said measurement zone for analysis of the fluid sample.

2. The method according to claim 1 wherein said flow delay material is a sizing material which slows absorption of fluids onto a surface for a predetermined time, and then permits complete flow of fluid through said porous substrate.

3. The method according to claim 2 wherein said sizing material is selected from the group consisting of alkyl ketene dimers, fluorocarbon polymers, and fatty acid chlorides.

4. The method according to claim 3 wherein said sizing delay material is selected from the group consisting of saturated fatty acid ketene dimers.

5. The method according to claim 4 wherein said ketene dimers are based on fatty acids having at least 14 carbon atoms.

6. The method according to claim 5 wherein said sizing material is palmitoyl ketene dimer.

7. The method according to claim 3 wherein said sizing material is a fatty acid chloride having at least 14 carbon atoms.

8. The method according to claim 3 wherein said sizing material is a fluorocarbon polymer.

9. The method according to claim 8 wherein said fluorocarbon polymer is substantially completely hydrophobic.

10. The method according to claim 8 wherein said fluorocarbon polymer is a copolymer having both hydrophilic and hydrophobic groups.

11. The method according to claim 1 wherein said porous substrate is a pad made of hydrophilic fibers.

12. The method according to claim 11 wherein said sizing material is present on the pad in an amount ranging from about about 0.001 microgram per pad to about 100 micrograms per pad.

13. The method according to claim 12 wherein said sizing material is a fluorocarbon polymer and said fluorocarbon polymer is present in an amount of from about 0.0005 microgram per pad to about 0.08 microgram per pad.

14. An assay device comprising a reagent layer, a flow delay layer below said reagent layer and a measurement zone below said flow delay layer, wherein said flow delay layer comprises a porous substrate coated or impregnated with a sizing material which retains a fluid in the porous substrate for a predetermined period of time and then permits the fluid to flow substantially completely through said porous substrate to said measurement zone for analysis of the fluid.

15. The device according to claim 14 wherein said sizing material is selected from the group consisting of alkyl ketene dimers, fluorocarbon polymers, and fatty acid chlorides.

16. The device according to claim 15 wherein said sizing material is an alkyl ketene dimer of a fatty acid having least 14 carbon atoms.

17. The device according to claim 16 wherein said porous substrate is first impregnated with lactose.

18. The device according to claim 16 wherein said sizing material is palmitoyl ketene dimer.

19. The device according to claim 16 wherein said sizing material is a fluorocarbon polymer.

20. The device according to claim 19 wherein said fluorocarbon polymer is substantially completely hydrophobic.

21. The device according to claim 19 wherein said fluorocarbon polymer is a copolymer having both hydrophilic and hydrophobic groups.

22. The device according to claim 14 wherein said porous substrate is a pad made of hydrophilic fibers.

23. The device according to claim 22 wherein said sizing material is present on the pad in an amount ranging from about about 0.001 microgram per pad to about 100 micrograms per pad.

24. The device according to claim 23 wherein said sizing material is a fluorocarbon polymer and said fluorocarbon polymer is present in an amount of from about 0.0005 microgram per pad to about 0.08 microgram per pad.

25. An assay device comprising an absorbent pad, a reagent layer below said absorbent pad, a flow delay layer below said reagent layer and a measurement zone below said flow delay layer, wherein said flow delay layer comprises a porous substrate coated or impregnated with a sizing material which retains a fluid in the porous substrate for a predetermined period of time and then permits the fluid to flow substantially completely through said porous substrate to said measurement zone for analysis of the fluid.

* * * * *